US008818824B2

(12) United States Patent
DeBusk et al.

(10) Patent No.: US 8,818,824 B2
(45) Date of Patent: Aug. 26, 2014

(54) AUTOMATED SYSTEM FOR MEDICAL ITEM DISPENSING, BILLING, AND INVENTORY MANAGEMENT

(75) Inventors: Brian C. DeBusk, Knoxville, TN (US); Angela M. Sewell, Knoxville, TN (US); John G. Jacobs, Knoxville, TN (US); Gregory S. Hodge, Knoxville, TN (US); Kevin E. Lynch, Knoxville, TN (US); William G. Pittman, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 329 days.

(21) Appl. No.: 13/223,641

(22) Filed: Sep. 1, 2011

(65) Prior Publication Data
US 2013/0060577 A1 Mar. 7, 2013

(51) Int. Cl.
*G06Q 50/00* (2012.01)
*G06Q 30/00* (2012.01)
(52) U.S. Cl.
CPC ............... *G06Q 30/00* (2013.01); *G06Q 50/00* (2013.01)
USPC ...................................... 705/3; 705/2; 705/28
(58) Field of Classification Search
CPC ..... G06Q 50/22; G06Q 50/24; G06Q 10/087; G06Q 10/08; G06F 19/3456; G06F 19/322; G06F 19/3462
USPC ................................... 705/2–3, 28
See application file for complete search history.

(56) References Cited

U.S. PATENT DOCUMENTS

| | | | | |
|---|---|---|---|---|
| 6,604,019 | B2 * | 8/2003 | Ahlin et al. | 700/231 |
| 2006/0259377 | A1 * | 11/2006 | Fedor et al. | 705/28 |
| 2009/0027164 | A1 * | 1/2009 | Hara | 340/10.1 |
| 2010/0094649 | A1 | 4/2010 | White | |
| 2010/0106515 | A1 * | 4/2010 | McCoy | 705/2 |
| 2010/0138238 | A1 * | 6/2010 | Sobie | 705/3 |
| 2010/0198611 | A1 * | 8/2010 | Ruoff et al. | 705/2 |
| 2010/0262432 | A1 * | 10/2010 | Benja-Athon | 705/2 |
| 2011/0010275 | A1 * | 1/2011 | Hull | 705/28 |
| 2011/0077969 | A1 * | 3/2011 | Zhu et al. | 705/3 |

OTHER PUBLICATIONS

Wavemark, Inc., Intelligent Storage Units & Usage Tracking, Brochure, pp. 1-2, USA, www.wavemark.net/website/documents/cabinetspecs.pdf.
Wavemark, Inc., Clinical Inventory Management Solution, Brochure, pp. 1-4, USA, www.wavemark.net/website/documents/wavemarkbrochure.pdf.

* cited by examiner

*Primary Examiner* — Sind Phongsvirajati
(74) *Attorney, Agent, or Firm* — Luedeka Neely Group, P.C.

(57) ABSTRACT

An inventory management system manages information regarding medical items dispensed in conjunction with medical treatment of a patient at a medical facility. The system includes a first computer, an inventory access control system, inventory sensors, and inventory applications in communication with the first computer. The inventory access control system receives credential information from a user seeking access to a physical inventory space in the medical facility and controls access to the space. The inventory sensors sense the removal of medical items to be dispensed to the patient, and generate item usage information indicating the identity and quantity of the items removed. The inventory applications associate the item usage information with patient information that identifies the patient to which the medical items are dispensed, thereby generating a record indicating that the items removed from the storage structure have been dispensed to the patient identified by the patient information.

18 Claims, 4 Drawing Sheets

AUTOMATED SYSTEM FOR MEDICAL ITEM DISPENSING, BILLING, AND INVENTORY MANAGEMENT

FIELD

This invention relates to an inventory management system. More particularly, this invention relates to a system for managing inventories of medical supply items.

BACKGROUND

Durable Medical Equipment (DME), Prosthetics, Orthotics and Supplies (DMEPOS) as defined by the Department of Health and Human Services and its Center for Medicare Services (CMS) is a class of medical devices, products and supplies that are typically reimbursable under Part B of the U.S. Medicare health care program. In general, this category of products includes items provided to patients who receive outpatient treatment for certain health problems that do not require inpatient admission to a hospital or other healthcare institution. DMEPOS items are typically provided or prescribed to help alleviate, treat or assist in recovery from the condition that prompted the outpatient treatment of the patient. Such outpatient treatment can occur in any number of settings, such as a hospital emergency department, a clinic, or a physician's or therapist's office.

In general, the costs of DMEPOS items are reimbursable or payable separately from the healthcare professional's fee for treatment of the patient. DMEPOS items are typically reimbursable or payable in both Medicare and Medicaid programs and through private health insurers. Traditionally, most DMEPOS items were prescribed by the treating professional and those prescriptions could be filled by DME shops, Orthotics/Prosthetics shops, pharmacies with DME services, etc. However, as a convenience to patients many healthcare providers would like to dispense DMEPOS items at the time of treatment of the patient in order to facilitate patient convenience and continuity of care.

Since DMEPOS items are typically reimbursable or payable under a different billing and reimbursement system than professional healthcare services, it has been difficult for healthcare professionals to provide the dispensing of these items as an adjunct service to their patients. The specialty shops that have traditionally dispensed these items have developed the business processes necessary to properly stock the products, manage the inventory, properly associate prescriptions for DMEPOS items with appropriate coding under the CMS coding system, generate the regulatory paperwork for delivery of the item to the patient and generate the necessary forms for submission to the reimbursement agency such as Medicare, Medicaid, or private insurance.

Healthcare providers have a need to dispense DMEPOS items as an adjunct service to their medical practice, without having to individually develop all of the business processes which suppliers have developed previously and without the labor and overhead costs associated with those types of suppliers. Healthcare providers need to be able supply the patient with DMEPOS products that the healthcare provider has evaluated and knows to be appropriate for the patient's particular diagnosis and indications. It would be a significant advantage for the patient if the healthcare provider could provide the DMEPOS item at the time of initial diagnosis and treatment of the patient. This would allow the healthcare provider to properly fit the item to the patient and instruct the patient on the proper use of the item. For the patient, this would minimize the hassle of having to go to other locations to complete the diagnosis and treatment, and would generally result in better continuity of care.

SUMMARY

The above and other needs are met by an integrated and automated medical product/supply dispensing, billing and inventory management system for use in the health care environment. The system includes several core functional software applications that communicate either through a networked information system architecture, or which reside on a single, general purpose computer workstation. In addition to the information system applications, the system includes a product/supply inventory management system which in general provides limited access to certain medical products or supplies and captures key information in the course of dispensing those products or supplies that subsequently enables the inventory management and billing functions of the system to operate.

In one preferred embodiment, an inventory management system manages information regarding medical items dispensed in conjunction with medical treatment of a patient at a medical facility. The inventory management system includes a first computer associated with the medical facility, an inventory access control system in communication with the first computer, one or more inventory sensors in communication with the first computer, and one or more inventory applications in communication with the first computer. The inventory access control system controls access to a physical inventory space in the medical facility in which an inventory of the medical items are disposed on or in a storage structure. The inventory access control system also receives credential information from a user seeking access to the physical space. The inventory sensors sense the removal of medical items from the storage structure to be dispensed to the patient, and generate item usage information indicative of the identity and quantity of the medical items removed. The inventory applications include computer-executable instructions which process the credential information to determine whether the user is authorized to enter the inventory space, and communicate with the inventory access control system to permit user entry when the credential information indicates that the user is so authorized. The computer-executable instructions also associate the item usage information with patient information that identifies the patient to which the medical items are dispensed, thereby generating a record indicating that the medical items removed from the storage structure have been dispensed to the patient identified by the patient information by the specific credentialed health care provider.

In some embodiments, one or more of the inventory applications are executed on the first computer. In some embodiments, one or more of the inventory applications are executed on a second computer that is in communication with the first computer through a communication network, and the credential information, item usage information, and patient information are communicated over the communication network.

In some embodiments, the inventory access control system includes a magnetic stripe reader, a proximity reader, a keypad, an RFID sensor, or a biometric sensor for receiving the credential information.

In some embodiments, the inventory sensors include weight sensors attached to the storage structure, an RFID sensor for sensing the presence of RFID tags attached to the medical items in the inventory space, or a bar code reader for scanning barcodes disposed on the medical items.

In some embodiments, the inventory management system includes an Electronic Medical Records (EMR) computer system associated with the medical facility and in communication with the first computer. The EMR computer system is configured to generate, receive, and process patient information.

In some embodiments, the inventory management system includes a patient billing computer system associated with the durable medical equipment (DME) supplier and in communication with the first computer. The patient billing computer system is configured to store and manage records regarding billing for services rendered and medical items dispensed to patients. In these embodiments, the inventory applications include computer-executable instructions which communicate the item usage information in association with the patient information to the patient billing computer system. In some embodiments, the patient billing computer system is in communication with a DME supplier's billing computer system, such as through a secure Internet connection.

Some embodiments include a display device connected to the first computer and viewable by the user. In these embodiments, the inventory applications include computer-executable instructions which cause the item usage information to be displayed on the display device for viewing by the user.

Some embodiments include an input device connected to the first computer for entering the patient information. In these embodiments, the inventory applications include computer-executable instructions which receive the patient information from the input device and cause the patient information to be displayed on the display device in association with the item usage information. The input device may be a keyboard on which the user may input the patent information, or a barcode reader for scanning a barcode on the patient's chart or touch screen.

In some embodiments, the inventory applications include computer-executable instructions which process the item usage information to update records indicating a count of medical items in inventory in the inventory space of the medical facility.

In some embodiments, the inventory management system includes a second computer associated with a service provider that provides medical items for replenishing the inventory of medical items in the inventory space of the medical facility. The second computer is in communication with the first computer via a communication network. An electronic data interchange server, which is in communication with the second computer, processes orders for medical items placed with the service provider. In these embodiments, the inventory applications include computer-executable instructions which process the item usage information to update records indicating a count of medical items in inventory in the inventory space of the medical facility, and determine that the count of medical items in inventory in the inventory space of the medical facility has dropped below a predetermined threshold. When the count has dropped below the predetermined threshold, the computer-executable instructions automatically place an order that is communicated through the communication network to the electronic data interchange server for medical items to replenish the inventory in the inventory space of the medical facility.

In another aspect, the invention provides an inventory management system for managing information regarding medical items dispensed in conjunction with medical treatment of a patient at a medical facility. The medical items are disposed on or in a storage structure in a physical inventory space in the medical facility. In one preferred embodiment, the inventory management system includes a first computer associated with the medical facility, one or more inventory sensors in communication with the first computer, and an input device in communication with the first computer. The inventory sensors sense removal of medical items from the storage structure to be dispensed to the patient, and generate item usage information indicative of an identity and quantity of the medical items removed. The input device is for entering patient information that identifies the patient to which the medical items are dispensed. The inventory applications include computer-executable instructions which receive the item usage information from the inventory sensors, receive the patient information from the input device, and generate a record associating the medical items identified by the usage information with the patient identified by the patient information.

In some embodiments, inventory applications include computer-executable instructions which determine whether the patient information has been entered, and generate a reminder message to remind appropriate personnel associated with the medical facility to input the patient information. This reminder message may be generated while a user is still present in the inventory space or after the user has exited the inventory space. If the reminder message is communicated before the user has exited the physical inventory space, the reminder message may comprise an audible communication or a visual communication or both. If the reminder message is communicated after the user has exited the physical inventory space, the reminder message may comprise a text message and/or an email message sent to the appropriate personnel associated with the medical facility

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 4:
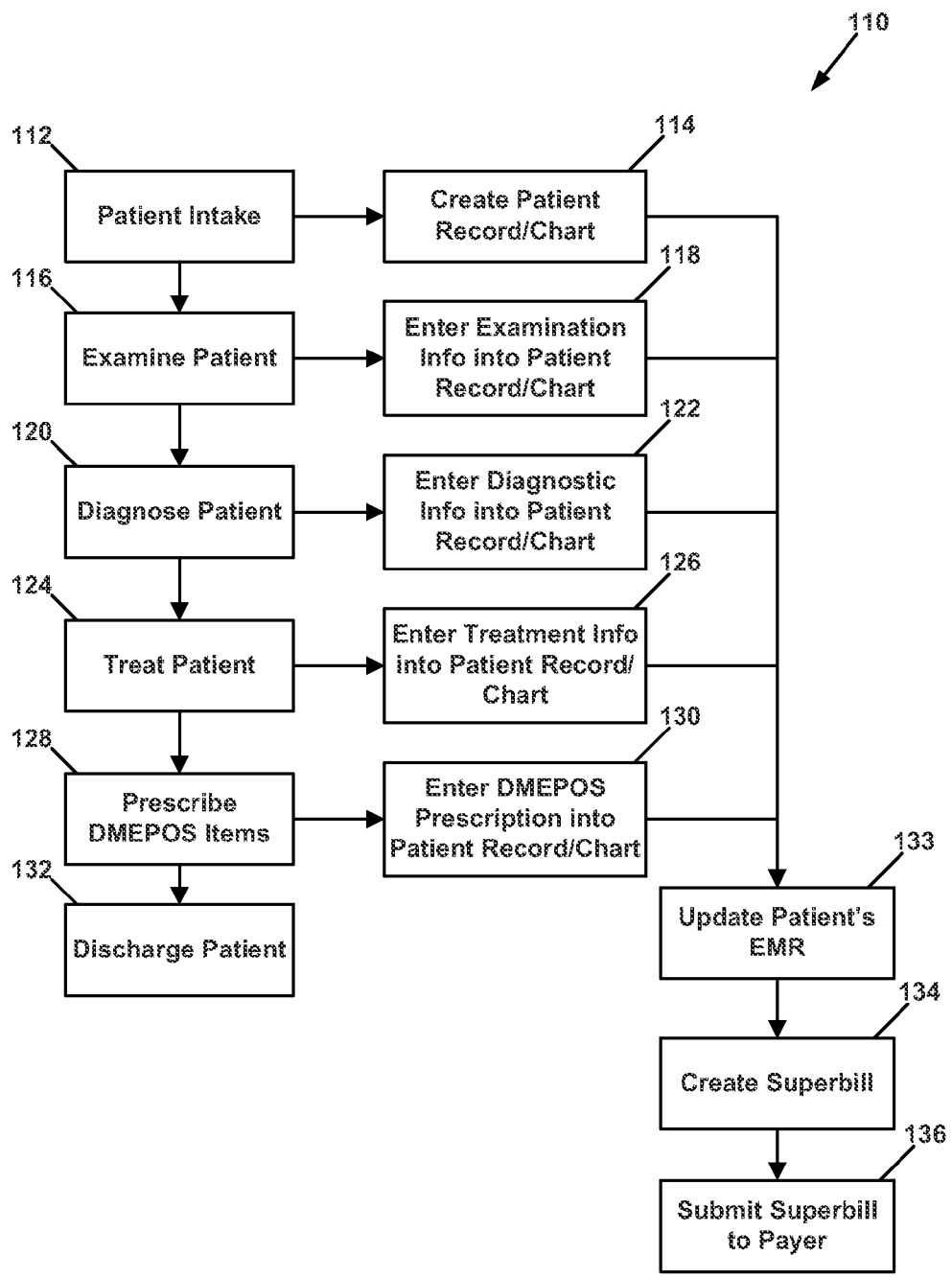
FIG. 4 depicts a typical workflow for the provision of DMEPOS items based on traditional practices.

A typical workflow for the provision of DMEPOS items under traditional practices is depicted in FIG. 4. Generally, a patient follows a treatment path 110 which typically begins with the patient arriving at a treatment facility with a medical condition and ends with the patient being discharged or leaving the treatment facility. Examples of treatment facilities include a hospital emergency department, a physician's office, a clinic, and a therapy office. The first step in the treatment path 110 is typically patient intake (step 112) in which information concerning the patient is recorded and a patient record/chart (or face sheet) is created as an output (step 114). Typically, patient intake (step 112) includes collecting of basic demographic and medical information about the patient, as well as payment responsibility information, such as insurance information (either private insurance or information regarding participation in a government program such as Medicare/Medicaid). This information is recorded in the patient record/chart, which is typically created in electronic form in a pre-existing information system resident in the treatment facility.

Following patient intake (step 112) is the examination of the patient(step 116). In this step, the appropriate healthcare provider examines the patient, takes a patient history, and reviews the symptoms. The examination (step 116) may also include other diagnostic activities such as lab work and imaging that assist the provider in making an accurate diagnosis. Examination information is typically recorded into the patient record/chart (step 118). The healthcare provider then makes a diagnosis of the patient (step 120), and the diagnostic information is also entered into the patient record/chart (step 122).

After diagnosis (step 120) and entering the diagnostic information in the patient record/chart (step 122), the next step is typically treatment of the patient (step 124). In the context of this invention, treatment of the patient typically includes the healthcare provider prescribing or providing a DMEPOS item, such as an orthotic, to facilitate treatment of the diagnosed condition (step 128). Information regarding the treatment, including DMEPOS prescription information, is entered into the patient record/chart (steps 126 and 130), and this information is entered in the patient's Electronic Medical Records (step 133).

The final step in the treatment Path 110, is for the patient to be discharged or released (step 132). The information entered into the patient record/chart at each step in the treatment path 110 is used to supply information to create a medical complaint bill reflecting all of the billable services provided in the process (step 134). This information is then uploaded to the appropriate billing software for submittal to payer (step 136).

Figure 1:
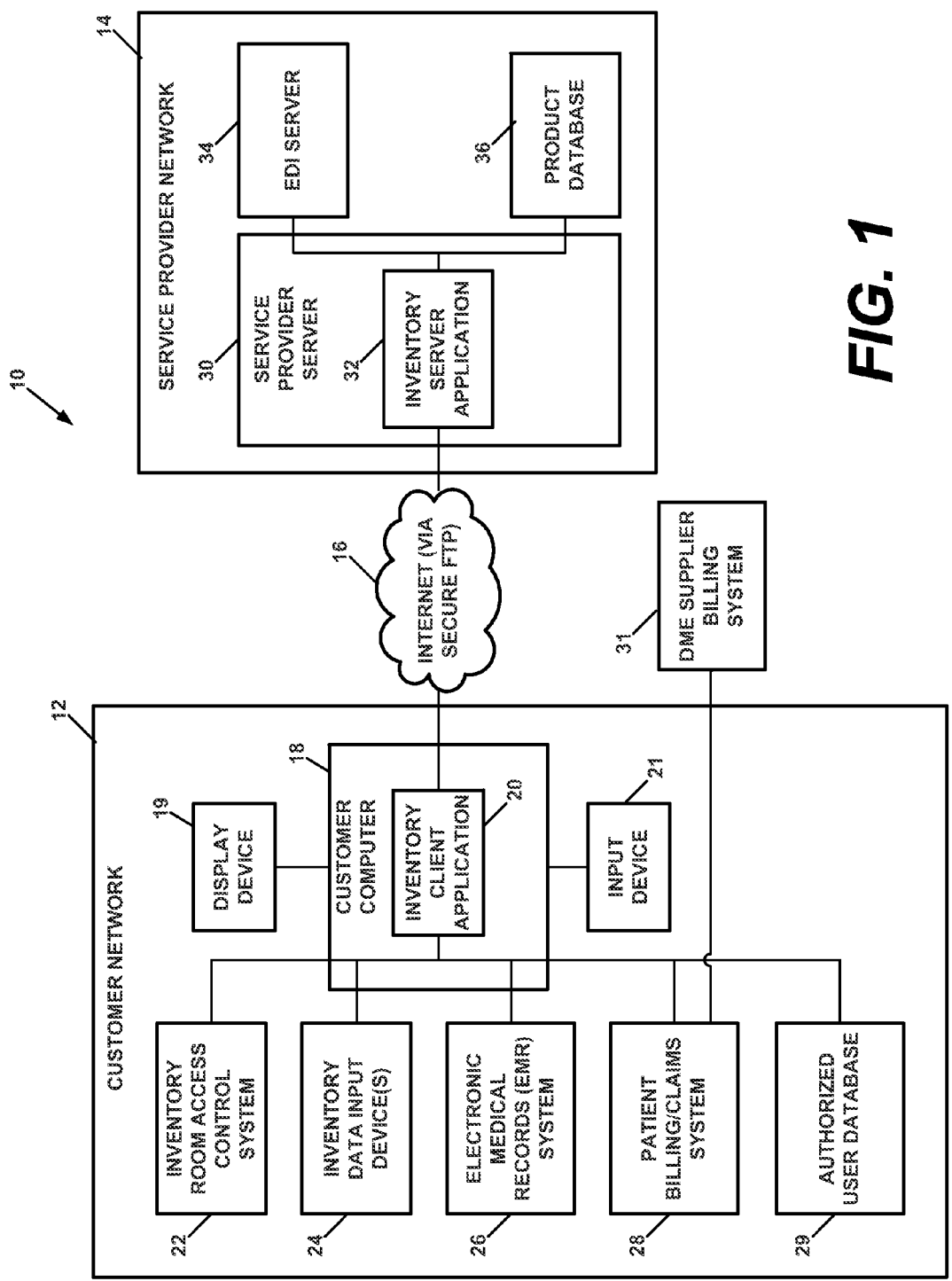
FIG. 1 is a functional block diagram of an embodiment of a medical product/supply dispensing, billing and inventory management system.

FIG. 1 depicts an embodiment of a medical product/supply dispensing, billing and inventory management system 10. As described in more detail hereinafter, the system 10 provides computer-implemented tools and processes for managing an inventory of medical products/supplies, for dispensing such products/supplies to patients, and for billing a payer for the dispensed products/supplies. However, one skilled in the art will recognize that the system 10 may be used to manage inventories of other components and materials in medical and nonmedical applications. Thus, the inventions described herein are not limited only to medical product/supply inventory, dispensing, and billing applications.

As shown in FIG. 1, the system 10 includes a customer computer network 12 and a service provider computer network 14 which communicate with each other via a communication network 16 such as the Internet. As the term is used herein, "customer" generally refers to a medical facility where medical diagnostic and treatment procedures are performed, such as a hospital, outpatient surgical center, physician's office, clinic, or therapy office. The term "customer" may also refer to any consumer of products/supplies that are inventoried and managed using the system described herein. Accordingly, one or more of the components of the customer computer network 12 may be located within a hospital, clinic, doctor's office, or other medical facility.

The customer computer network 12 includes a customer computer 18, also referred to herein as a first computer, that is operable to communicate through the Internet 16 with the service provider computer network 14. The customer computer 18 may be, for example, a desktop computer, laptop computer, tablet computer, or smart phone. An inventory client application 20 is loaded on the customer computer to provide some or all of the inventory management, dispensing, and billing functions described herein. The customer computer 18 and the client application 20 are in communication with an inventory room access control system 22, one or more inventory sensors 24, an Electronic Medical Records (EMR) computer system 26, and a patient billing/claims computer system 28. A user input device 21, such as a keyboard or mouse or touchpad, is preferably provided as a component of the customer computer 18. In a preferred embodiment, the customer computer 18 also includes a display device 19 within the inventory room on which the inventory client application 20 displays information regarding inventory transactions. In some embodiments, the display device 19 and user input device 21 are combined as a touch screen device.

The inventory room access control system 22 comprises a keypad, magnetic stripe reader (card swipe), proximity reader, RFID tag reader, biometric sensor device, or other entry-access device that authorized customer personnel use to gain access to a medical product/supply inventory room. The inventory room may be a secured, limited-access location in the customer facility in which DMEPOS items are stored. In preferred embodiments, the access control system 22 communicates with the customer computer 18 via a wired or wireless network connection.

The inventory sensors 24 are devices which sense the removal or addition of DMEPOS items from or to inventory within the inventory room. In one embodiment, the inventory sensors 24 are weight sensors attached to storage bins within the inventory room. In this embodiment, the inventory sensors 24 sense that one or more items have been added to a bin based on an increase in weight of the bin, and that one or more items have been removed from the bin based on a decrease in weight of the bin. With this system, particular bins are designated to hold particular items, so that a change in weight of the bin can be associated with a change in inventory of the corresponding item.

In another embodiment, the inventory sensors 24 are RFID sensors which sense the presence of RFID tags attached to DMEPOS items within the inventory room. When an RFID tag on an item is within range of the RFID sensors, the tagged item is designated as being in inventory. Conversely, when the RFID tag on an item is outside the range of the RFID sensors, the tagged item is designated as being removed from inventory. In this embodiment, since the RFID tags identify the items to which they are attached, there is no need to designate particular bins or locations for each item within the inventory room.

In another embodiment, the inventory sensors 24 are RFID sensors which sense the presence of RFID tags attached to DMEPOS items when in range of the sensors. When an RFID tag on an item is within range of the RFID sensors, the tagged item is designated as being removed from inventory. Conversely, when the RFID tag on an item is outside the range of the RFID sensors, the tagged item is designated as being in inventory. In this embodiment, since the RFID tags identify the items to which they are attached, there is no need to designate particular bins or locations for each item within the inventory room.

In the embodiments discussed above, the inventory sensors 24 are substantially automatic. That is, they detect the addition and removal of items to and from inventory without human interaction. In a third embodiment, human interaction is required. In this embodiment, the inventory sensors 24 are barcode readers, and when a DMEPOS item is added to or removed from inventory, this is logged by scanning a barcode attached to the item.

The EMR computer system 26 comprises one or more computers that store and manage records regarding the status of patients receiving treatment in a medical facility. Generally, a patient's status is either admitted to the facility, discharged from the facility, or transferred to another department, location or facility.

The billing/claims computer system 28 comprises one or more computers that store and manage records regarding the billing for services rendered and DMEPOS items dispensed in examining, diagnosing, and treating patients. In preferred embodiments, this system 28 generates bills (in paper or electronic form) which are sent to patients, and generates claims which are sent to private insurers and Medicare/Medicaid. In some embodiments, the billing/claims computer system 28 is operable to communicate with a DMEPOS supplier's billing computer system 31 such as through a secure Internet connection.

With continued reference to FIG. 1, the service provider computer network 14 comprises one or more computers which store information and execute software for medical product/supply dispensing, billing and inventory management. As the term is used herein, a "service provider" may be a company that maintains inventories of DMEPOS items that are supplied to the customer to be dispensed to patients. An example of one such service provider is DeRoyal Industries, Inc. of Powell, Tenn. Alternatively, the "service provider" may not maintain the inventory, but may provide inventory management services for another company that does maintain the inventory.

In the embodiment of FIG. 1, the service provider computer network 14 includes an inventory management server computer 30, also referred to herein as a second computer, running an inventory server application 32, an electronic data interchange (EDI) server 34, and a product inventory database 36. The EDI server 34, which may be a J. D. Edwards/Oracle server, executes programs for implementing electronic commerce transactions between the service provider network 14 and the customer network 12. The product inventory database 36 stores records indicating quantities, coding, use and application of each DMEPOS item in the service provider's inventory.

Figure 2:
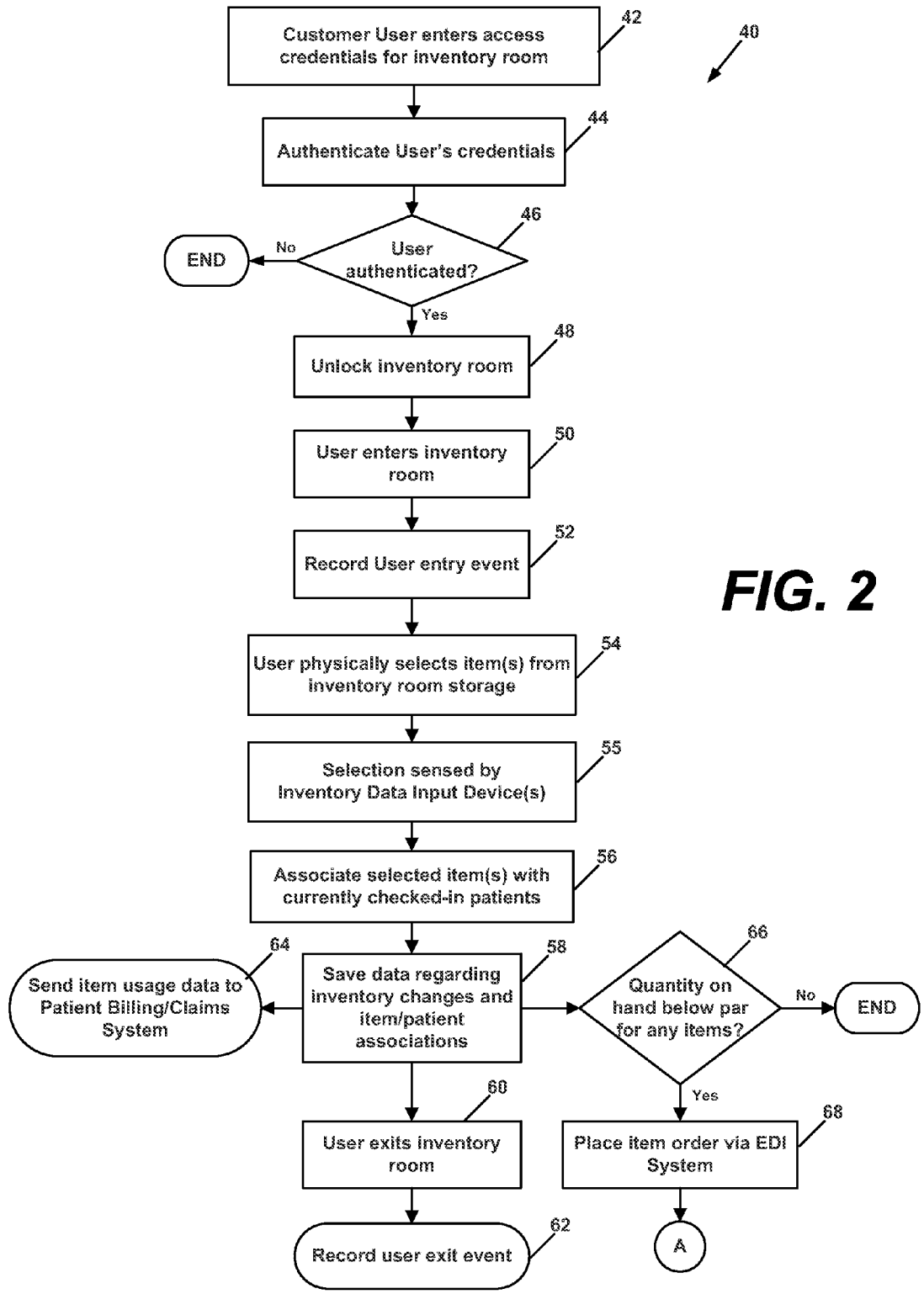
FIGS. 2 and 3 are flowcharts describing the operation of an embodiment of a medical product/supply dispensing, billing and inventory management system.

FIG. 2 depicts a process 40 for providing access to DMEPOS items in the inventory room of the customer facility, for logging removal of inventory items, and for billing the patient accordingly. Generally, the process 40 begins when a customer user enters credentials for gaining access to the inventory room (step 42). In one embodiment, this is accomplished by swiping a magnetic stripe on an ID card through a card reader of the inventory room access control system 22 (FIG. 1). In another embodiment, this is accomplished by swiping a proximity card near a proximity reader. In another embodiment, this involves passing an RFID tag near an RFID reader. In another embodiment, this involves entering a code on a keypad. In yet another embodiment, this involves a retina scan or a thumbprint scan using a biometric scanning device.

After entry of the customer user's credentials, the inventory client application 20 running on the customer computer 18 authenticates the credentials (step 44), such as by comparing the credentials to records saved in an authorized user database 29. The authorized user database 29 may be maintained on the customer network 12.

If the user's credentials are not authenticated (step 46), the door of the inventory room remains locked and no further action is taken, other than to log a failed entry attempt. If the user's credentials are authenticated, the inventory client application 20 executes a command to unlock the inventory room door (step 48) and the user may enter the inventory room (step 50). The inventory client application 20 then updates a user entry log to record this user entry event, with the date and time of entry and the name/ID number of the user (step 52). Additionally, the user is logged into the application 20.

When the user selects one or more items from the shelves, bins, or drawers of the inventory room (step 54), the selection is sensed by one or more of the inventory sensors 24 and corresponding selection data is provided to the inventory client application 20 (step 55). In a preferred embodiment, a list of the selected items is then displayed on the display screen 19 for viewing by the user. Using the input device 21, the user inputs information that the inventory client application 20 uses to associate each selected item with a currently admitted or checked-in patient in the facility (step 56). To input this information, the user may select the patient's name from a list displayed on the display device 19, which list is generated from data accessed from the EMR computer system 26. Alternatively, the user may scan a barcode assigned to the patient which is attached to the patient's paperwork. In other embodiments, the patient is associated with the selected DMEPOS item by patient information included in RFID tag on the patient's chart.

The inventory client application 20 saves data regarding the removal of items from inventory (also referred to as item usage data) and data indicating the item/patient association (step 58). The item usage data and item/patient association data are sent to the patient billing/claims computer system 28 for further processing (step 64). For example, the patient billing/claims computer system 28 may use this data to submit claims for payment to appropriate insurance providers.

Based on the item usage data, the inventory client application 20 determines whether the remaining quantity of inventory items is below a predetermined minimum threshold (step 66). If so, the inventory client application 20 places an order for some quantity of the items via the Internet connection to the service provider's EDI server 34 (step 68).

After the user has associated the items taken from inventory with one or more patients (step 56), the user may exit the inventory room (step 60) and the inventory client application 20 logs a user exit event (step 62). In some embodiments, the inventory room door may not be opened to allow the user to exit until the user has done whatever is needed to complete item/patient association (step 56). In other embodiments, the door may be opened, but if the item/patient association has not been completed beforehand, an alarm sounds to remind the user to complete that task before leaving. In some embodiments, if the user leaves the inventory room without completing the item/patient association, the user will receive an email or text message reminding the user to complete the task.

By logging user entry and exit events, the system 10 keeps track of all users that visit the inventory room, and it associates the items removed from or added to inventory with the dates/times of each user's visit to the inventory room. This provides for user accountability in the inventory process.

Figure 3:
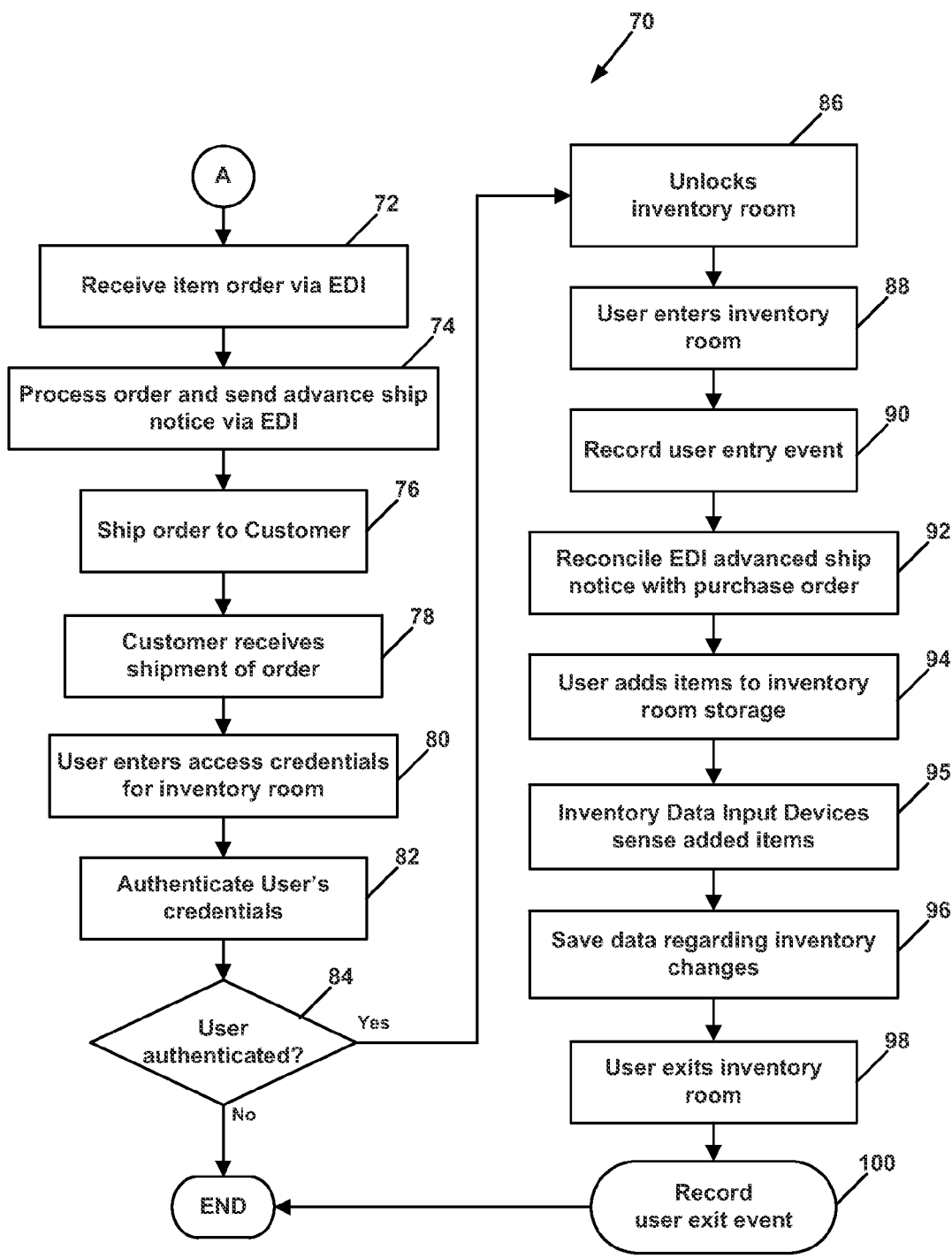

FIG. 3 depicts a preferred embodiment of a process 70 for replenishing items in the inventory room of the customer facility. Initially, the service provider's inventory server application 32 receives the order for items (step 72) that was placed by the inventory client application 20 in step 68 of FIG. 2. The inventory server application 32 passes the order to the EDI server 34. The EDI server 34 processes the order and sends an advance ship notice to the customer via the inventory server application 32 (step 74). The service provider then ships the ordered items (step 76) and the customer receives the ordered items (step 78). The customer user then takes the received items to the inventory room to restock the inventory. The customer user enters credentials for gaining access to the inventory room (step 80), such as by swiping a magnetic stripe on an ID card through a card reader of the inventory room access control system 22. The inventory client application 20 running on the customer computer 18 authenticates the user's credentials (step 82) as described above.

If the user's credentials are not authenticated (step 84), the door of the inventory room remains locked and no further action is taken, other than to log a failed entry attempt. If the user's credentials are authenticated, the inventory client application 20 executes a command to unlock the inventory room door (step 86) and the user may enter the inventory room (step 88). The inventory client application 20 then updates a user entry log to record this user entry event, with the date and time of entry and the name/ID number of the user (step 90). Alternatively or in addition, the inventory server application 32 may update a user entry log maintained on the service provider server 30.

The user reconciles the EDI advance ship notice with the purchase order that was issued in step 68 of FIG. 2 (step 92) and physically adds the received items to the appropriate bins, shelves, or drawers in the inventory room (step 94). When the user adds one or more items to the shelves, bins, or drawers, the addition is automatically sensed by one or more of the inventory sensors 24 (such as by sensing additional weight in a bin or by sensing the presence of previously unlogged RFID tags on the added items) and the corresponding replenishment data is provided to the inventory client application 20 (step 95). The inventory client application 20 records the data indicating an addition of items to inventory (step 96). In a preferred embodiment, a list of the added items is displayed on the display screen 19 for viewing, confirmation, and editing by the user. When the user exits the inventory room (step 98), the inventory client application 20 logs a user exit event (step 100).

It should be appreciated that many of the steps of FIGS. 2 and 3 may be performed by the inventory server application 32, by the inventory client application 20, or by both working together. Thus, the invention is not limited to performance of the process steps by any particular application or on any particular computer system.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An inventory management system for managing information regarding medical items dispensed in conjunction with medical treatment of a patient at a medical facility, wherein the medical items are disposed on or in a storage structure in a physical inventory space in the medical facility, the inventory management system comprising:
    a first computer associated with the medical facility;
    one or more inventory sensors in communication with the first computer, the one or more inventory sensors for sensing removal of one or more medical items from the storage structure to be dispensed to the patient, and for generating item usage information indicative of an identity and quantity of the one or more medical items removed;
    an input device in communication with the first computer, the input device for entering patient information that identifies the patient to which the one or more medical items are dispensed; and
    one or more inventory applications in communication with the first computer, the one or more inventory applications including:
        computer-executable instructions which, when executed, receive the item usage information from the one or more inventory sensors, receive the patient information from the input device, and generate a record associating the one or more medical items identified by the usage information with the patient identified by the patient information;
        computer-executable instructions which, when executed, determine whether the patient information has been entered; and
        computer-executable instructions which, when executed, generate a reminder message to remind appropriate personnel associated with the medical facility to input the patient information if it has not already been entered.

2. The system of claim 1 further comprising:
    an inventory access control system in communication with the first computer, the inventory access control system for monitoring personnel ingress to and egress from the physical inventory space; and
    the one or more inventory applications including computer-executable instructions which, when executed, determine whether the patient information has been entered before a user has exited the physical inventory space.

3. The system of claim 2 wherein the one or more inventory applications include computer-executable instructions which, when executed, generate the reminder message for communication to the user before the user has exited the physical inventory space, wherein the communication of the reminder message comprises one or more of an audible communication and a visual communication.

4. The system of claim 2 wherein the one or more inventory applications include computer-executable instructions which, when executed, generate the reminder message for communication after the user has exited the physical inventory space, wherein the communication of the reminder message comprises one or more of a text message and an email message sent to the appropriate personnel associated with the medical facility.

5. The system of claim 1 wherein the one or more inventory applications include computer-executable instructions which, when executed, communicate the item usage information and patient information to an Electronic Medical Records (EMR) system of the medical facility, and interact with the EMR system to generate discharge documentation for the patient that reflects the item usage information.

6. The system of claim 1 wherein the physical inventory space comprises an inventory room.

7. The system of claim 1 wherein the physical inventory space comprises a secured limited-access location.

8. The system of claim 1 wherein the one or more inventory sensors include one or more of:
    a weight sensor attached to the storage structure;
    an RFID sensor for sensing the presence of RFID tags attached to the medical items in the inventory space; and
    a bar code reader for scanning barcodes disposed on the medical items.

9. The system of claim 1 further comprising an Electronic Medical Records computer system associated with the medical facility and in communication with the first computer, the Electronic Medical Records computer system configured to generate, receive, and process patient information.

10. The system of claim 1 further comprising:
a patient billing computer system associated with the medical facility and in communication with the first computer, the patient billing computer system configured to store and manage records regarding billing for services rendered and medical items dispensed to patients; and
the one or more inventory applications including computer-executable instructions which, when executed, communicate the item usage information in association with the patient information to the patient billing computer system.

11. The system of claim 1 further comprising:
a display device connected to the first computer and viewable by the user; and
the one or more inventory applications including computer-executable instructions which, when executed, cause the item usage information to be displayed on the display device for viewing by the user.

12. The system of claim 11 wherein the one or more inventory applications include computer-executable instructions which, when executed, receive the patient information from the input device and cause the patient information to be displayed on the display device in association with the item usage information.

13. The system of claim 1 wherein the input device comprises one or more of a keyboard and touch screen on which the user may input the patent information.

14. The system of claim 1 wherein the input device comprises a barcode reader for scanning a barcode on a patient's chart.

15. The system of claim 1 wherein the one or more inventory applications include computer-executable instructions which, when executed, process the item usage information to update records indicating a count of medical items in inventory in the inventory space of the medical facility.

16. The system of claim 1 further comprising:
a second computer associated with a service provider that provides medical items for replenishing the inventory of medical items in the inventory space of the medical facility, the second computer in communication with the first computer via a communication network; and
an electronic data interchange server in communication with the second computer, the electronic data interchange server for processing orders for medical items placed with the service provider.

17. The system of claim 16 wherein the one or more inventory applications include:
computer-executable instructions which, when executed, process the item usage information to update records indicating a count of medical items in inventory in the inventory space of the medical facility;
computer-executable instructions which, when executed, determine that the count of medical items in inventory in the inventory space of the medical facility has dropped below a predetermined threshold; and
computer-executable instructions which, when executed, automatically place an order communicated through the communication network to the electronic data interchange server for medical items to replenish the inventory in the inventory space of the medical facility when the count has dropped below the predetermined threshold.

18. An inventory management system for managing information regarding medical items dispensed in conjunction with medical treatment of a patient at a medical facility, the inventory management system comprising:
a first computer associated with the medical facility;
an inventory access control system in communication with the first computer, the inventory access control system for controlling access to a physical inventory space in the medical facility in which an inventory of the medical items are disposed on or in a storage structure, the inventory access control system further for receiving credential information from a user seeking access to the physical space;
one or more inventory sensors in communication with the first computer, the one or more inventory sensors for sensing removal of one or more medical items from the storage structure to be dispensed to the patient, and for generating item usage information indicative of an identity and quantity of the one or more medical items removed;
a display device disposed within the physical inventory space and connected to the first computer and viewable by the user;
an input device disposed within the physical inventory space and connected to the first computer, the input device for entering patient information regarding a patient for which the one or more medical items are to be dispensed; and
a patient billing computer system associated with the medical facility and in communication with the first computer, the patient billing computer system configured to store and manage records regarding billing for services rendered and medical items dispensed to patients; and
one or more inventory applications in communication with the first computer, the one or more inventory applications including:
computer-executable instructions which, when executed, process the credential information to determine whether the user is authorized to enter the inventory space, and communicate with the inventory access control system to permit user entry into the inventory space when the credential information indicates that the user is so authorized;
computer-executable instructions which, when executed, determine whether the patient information has been entered in association with the item usage information;
computer-executable instructions which, when executed, generate a reminder message for display on the display device to remind the user to input the patient information if the patient information has not been entered before the user proceeds to exit the inventory space;
computer-executable instructions which, when executed, receive the patient information from the input device;
computer-executable instructions which, when executed, associate the item usage information with patient information that identifies the patient to which the one or more medical items are dispensed, thereby generating a record indicating that the one or more medical items removed from the storage structure are dispensed to the patient identified by the patient information;
computer-executable instructions which, when executed, cause the item usage information and patient information to be displayed on the display device for viewing by the user;

computer-executable instructions which, when executed, communicate the item usage information in association with the patient information to the patient billing computer system; and computer-executable instructions which, when executed, process the item usage information to update records indicating a count of medical items in inventory in the inventory space of the medical facility.

\* \* \* \* \*